United States Patent [19]

Berg et al.

[11] Patent Number: 4,859,285

[45] Date of Patent: * Aug. 22, 1989

[54] SEPARATION OF 2-PENTANONE FROM FORMIC ACID BY EXTRACTIVE DISTILLATION

[75] Inventors: Lloyd Berg, 1314 S. Third Ave., Bozeman, Mont. 59715; Rudolph J. Szabados; Thomas H. Flower, both of Bozeman, Mont.

[73] Assignee: Lloyd Berg, Bozeman, Mont.

[*] Notice: The portion of the term of this patent subsequent to Dec. 27, 2005 has been disclaimed.

[21] Appl. No.: 189,054

[22] Filed: May 2, 1988

[51] Int. Cl.[4] .................. B01D 3/40; C07C 45/83; C07C 51/44

[52] U.S. Cl. ........................... 203/51; 203/56; 203/60; 203/61; 203/62; 203/64; 562/609; 568/410

[58] Field of Search .............. 203/51, 62, 61, 60, 203/64, 63, 56; 568/410; 562/609

[56] References Cited

U.S. PATENT DOCUMENTS

| | | | |
|---|---|---|---|
| 2,010,384 | 8/1935 | van Melsen et al. | 568/410 |
| 2,269,163 | 1/1942 | Othmer | 203/51 |
| 2,586,929 | 2/1952 | Fleming et al. | 568/410 |
| 3,013,954 | 12/1961 | Pacoud et al. | 203/62 |
| 3,265,592 | 8/1966 | Van der Weel | 568/410 |

*Primary Examiner*—Wilbur Bascomb

[57] ABSTRACT

2-Pentanone cannot be completely removed from 2-pentanone and formic acid mixtures by distillation because of the presence of the maximum azeotrope. 2-Pentanone can be readily removed from 2-pentanone-formic acid mixtures by extractive distillation in which the extractive agent is a ketone, either alone or mixed with certain high boiling organic compounds. Examples of effective agents are cyclohexanone; diisobutyl ketone and octanoic acid; isophorone, hexanoic acid and butyl ether.

10 Claims, No Drawings

SEPARATION OF 2-PENTANONE FROM FORMIC ACID BY EXTRACTIVE DISTILLATION

FIELD OF THE INVENTION

This invention relates to a method for separating formic acid from 2-pentanone using certain higher boiling liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation of each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

Formic acid, B.P. = 100.8° C., and 2-pentanone, B.P. = 102.4° C. form a maximum azeotrope boiling at 105.5° C. and containing 32 wt.% formic acid. When these two are found together in mixtures, either alone or with other liquids, distillation will only produce the azeotrope, never pure formic acid or 2-pentanone Thus any liquid mixture containing these two will on distillation produce the azeotrope. Extractive distillation would be an attractive method of effecting the separation of formic acid from 2-pentanone if agents can be found that (1) will break the formic acid-2-pentanone azeotrope and (2) are easy to recover from the formic acid, that is, form no azeotrope with formic acid and boil sufficiently above formic acid to make the separation by rectification possible with only a few theoretical plates.

Extractive distillation typically requires the addition of an equal amount to twice as much extractive agent as the 2-pentanone and formic acid on each plate of the rectification column. The extractive agent should be heated to about the same temperature as the plate on which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the coat of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of 2-pentanone to formic acid in their separation in a rectification column. It is a further object of this invention to identify suitable extractive distillation agents which will eliminate the 2-pentanone-formic acid azeotrope and make possible the production of pure 2-pentanone and formic acid by rectification. It is a further object of this invention to identify organic compounds which in addition to the above constraints, are stable, can be separated from formic acid by rectification with relatively few theoretical plates and can be recycled to the extractive distillation column and re-used with little or no decomposition.

SUMMARY OF THE INVENTION

The objects of the invention are provided by a process for separating 2-pentanone from formic acid which entails the use of certain oxygenated organic compounds as the agent in extractive distillation.

DETAILED DESCRIPTION OF THE INVENTION

We have discovered that certain ketones, either alone or admixed with other high boiling organic compounds, will effectively negate the 2-pentanone-formic acid maximum azeotrope and permit the separation of 2-pentanone from formic acid by rectification when employed as the agent in extractive distillation. Table 1 lists the ketones and their mixtures and the approximate proportions that we have found to be effective.

TABLE 1

Extractive Distillation Agents Which Are Effective In Breaking The 2-Pentanone - Formic Acid Azeotrope

| Compounds | Ratios | | Relative Volatility | |
|---|---|---|---|---|
| Cyclohexanone | 1 | 6/5 | 4.1 | 2.9 |
| Isophorone | " | " | 3.4 | 2.2 |
| Diisobutyl ketone | " | " | 1.5 | 1.6 |
| Ethyl butyl ketone | " | " | 1.5 | 1.4 |
| Methyl isoamyl ketone | " | " | 1.2 | 1.2 |
| 2-Heptanone | " | " | 2.6 | 1.4 |
| 2-Octanone | " | " | 1.4 | 1.4 |

TABLE 1-continued
Extractive Distillation Agents Which Are Effective In Breaking The 2-Pentanone - Formic Acid Azeotrope

| Compounds | Ratios | | Relative Volatility | |
|---|---|---|---|---|
| 2,4-Pentanedione | " | " | 1.2 | 1.1 |
| Acetonyl acetone | " | " | 2.3 | 3.0 |
| Cyclohexanone, Heptanoic acid | $(\frac{1}{2})^2$ | $(3/5)^2$ | 1.5 | 1.5 |
| Cyclohexanone, Isophorone | " | " | 3.2 | 2.4 |
| Cyclohexanone, Methyl salicylate | " | " | 1.4 | 1.4 |
| Isophorone, Hexanoic acid | " | " | 2.4 | 1.5 |
| Isophorone, Heptanoic acid | " | " | 1.3 | 2.0 |
| Isophorone, Methyl salicylate | " | " | 1.6 | 1.6 |
| Isophorone, Propiophenone | " | " | 1.5 | 2.3 |
| Diisobutyl ketone, Octanoic acid | " | " | 2.2 | 1.8 |
| Ethyl butyl ketone, Heptanoic acid | " | " | 1.4 | 1.4 |
| 2-Octanone, Malic acid | " | " | 1.6 | 1.4 |
| Isophorone, 2,4-Pentanedione | " | " | 1.6 | 1.7 |
| Isophorone, Acetonyl acetone | " | " | 2.1 | 2.1 |
| Cyclohexanone, Isophorone, Methyl benzoate | $(\frac{1}{3})^3$ | $(2/5)^3$ | 1.7 | 1.8 |
| Cyclohexanone, Isophorone, Diisobutyl ketone | " | " | 1.1 | 2.1 |
| Cyclohexanone, Isophorone, Methyl salicylate | " | " | 1.6 | 1.3 |
| Cyclohexanone, Hexanoic acid, Acetophenone | " | " | 2.1 | 1.3 |
| Cyclohexanone, Heptanoic acid, Methyl benzoate | " | " | 1.8 | 1.8 |
| Cyclohexanone, 2-Heptanone, Methyl salicylate | " | " | 1.1 | 1.1 |
| Isophorone, Hexanoic acid, Butyl ether | " | " | 2.1 | 1.5 |
| Isophorone, Heptanoic acid, Benzyl ether | " | " | 1.5 | 1.4 |
| Isophorone, Propiophenone, Diisobutyl ketone | " | " | 1.1 | 1.5 |
| Isophorone, 2,4-Pentanedione, Adiponitrile | " | " | 2.4 | 1.7 |
| Isophorone, Acetonyl acetone, Dipropylene glycol dibenzoate | " | " | 1.5 | 1.5 |
| Ethyl butyl ketone, n-Decanoic acid, Diethylene glycol dimethyl ether | " | " | 1.6 | 1.1 |

The data in Table 1 was obtained in a vapor-liquid equilibrium still. In every case, the starting material was the 2-pentanone-formic acid azeotrope. The ratios are the parts by weight of extractive agent used per part of 2-pentanone-formic acid azeotrope. The relative volatilities are listed for each of the wto ratios employed. The ketones which are effective when used alone are cyclohexanone, isophorone, diisobutyl ketone, ethyl butyl ketone, methyl isoamyl ketone, 2-heptanone, 2-octanone, 2,4-pentanedione and acetonyl acetone. The compounds which are effective when used in mixtures with above listed ketones are hexanoic acid, heptanoic acid, pelargonic acid, octanoic acid, malic acid, n-decanoic acid, methyl benzoate, methyl salicylate, propiophenone, acetophenone, butyl ether, benzyl ether, adiponitrile, diethylene glycol dimethyl ether and dipropylene glycol dibenzoate.

The two relative volatilities shown in Table 1 correspond to the two different ratios investigated. For example, in Table 1, one part of cyclohexanone mixed with one part of the 2-pentanone-formic acid azeotrope gives a relative volatility of 4.1; with 6/5 parts of cyclohexanone, the relative volatility is 2.9. One half part of cyclohexanone mixed with one half part of heptanoic acid with one part of the 2-pentanone-formic acid azeotrope gives a relative volatility of 1.5; 3/5 parts of cyclohexanone plus 3/5 parts of heptanoic acid give 1.5. One third part of cyclohexanone plus ⅓ part of isophorone plus ⅓ part of methyl benzoate with one part of the 2-pentanone-formic acid azeotrope gives a relative volatility of 1.7; with 2/5 parts, these three give a relative volatility of 1.8. In every example in Table 1, the starting material is the 2-pentanone-formic acid azeotrope which possesses a relative volatility of 1.00.

Several of the mixtures listed in in Table 1 and whose relative volatility had been determined in the vapor-liquid equilibrium still, was then evaluated in a glass perforated plate rectification column possessiing 4.5 theoreti-

TABLE 2
Data From Runs Made In Rectification Column

| Agent | Column | Time, hrs. | Weight % 2-Pentanone | Weight % Formic acid | Relative Volatility |
|---|---|---|---|---|---|
| 50% Cyclohexanone, 50% Isophorone | Overhead | ½ | 98.8 | 1.2 | 2.63 |
| | Bottoms | | 50.5 | 49.5 | |
| | Overhead | 1 | 97.3 | 2.7 | 2.33 |
| | Bottoms | | 45 | 55 | |
| 33% Cyclohexanone, 33% Isophorone, 33% Methyl benzoate | Overhead | ½ | 96.9 | 3.1 | 1.34 |
| | Bottoms | | 45.9 | 54.1 | |
| | Overhead | 1 | 97.8 | 2.2 | 1.39 |
| | Bottoms | | 50 | 50 | |
| | Overhead | 1.5 | 98.8 | 1.2 | 1.49 |
| | Bottoms | | 57.4 | 42.6 | |
| 50% Diisobutyl ketone, 50% Pelargonic acid | Overhead | ½ | 75.8 | 24.2 | 1.30 |
| | Bottoms | | 48.3 | 51.7 | |
| | Overhead | 1 | 86.5 | 13.5 | 1.45 |
| | Bottoms | | 53.2 | 46.8 | |
| | Overhead | 2 | 88 | 12 | 1.48 |
| | Bottoms | | 55.5 | 44.5 | | cal plates and then results listed in Table 2. The data in Table 2 was obtained in the following manner. The charge was 250 grams of the 2-pentanone-formic acid azeotrope and after a half hour of operation in the 4.5 theoretical plate column to establish equilibrium, 33% cyclohexanone, 33% isophorone and 33% methyl benzoate at 95° C. and 20 ml/min. was pumped in. The rectification was continued with sampling of the overhead and bottoms after one half hour. The analyses are shown in Table 2 and were 96.9% 2-pentanone, 3.1% formic acid in the overhead and 45.9% 2-pentanone, 54.1% formic acid in the bottoms which gives a relative volatility of 1.34 of 2-pentanone to formic acid. After one hour of continuous operation, the overhead was 97.8% 2-pentanone, 2.2% formic acid and the bottoms was 50% 2-pentanone, 50% formic acid which is a relative volatility of 1.39. After 1.5 hours of continuous operation, the overhead was 98.8% 2-pentanone, 1.2% formic acid and the bottoms was 57.4% 2-pentanone, 42.6% formic acid which is a relative volatility of 1.49. This proves that the extractive distillation agent is negating the azeotrope and makes the rectification proceed as if the azeotrope no longer existed and brings out the pure 2-pentanone as overhead.

THE USEFULNESS OF THE INVENTION

The usefulness or utility of this invention can be demonstrated by referring to the data presented in Tables 1 and 2. All of the successful extractive distillation agents show that 2-pentanone and formic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boiling rate low enough to make this a useful and efficient method of recovering high purity 2-pentanone and formic acid from any mixture of these two including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the 2-pentanone-formic acid azeotrope and 50 grams of cyclohexanone were charged to a vapor-liquid equilibrium still and refluxed for twelve hours. Analysis indicated a vapor composition of 77.7% 2-pentanone, 22.3% formic acid, a liquid composition of 46% 2-pentanone, 54% formic acid which is a relative volatility of 4.1 Ten grams of cyclohexanone were added and refluxing continued for another seven hours. Analysis indicated a vapor composition of 80% 2-pentanone, 20% formic acid, a liquid composition of 57.7% 2-pentanone, 42.3% formic acid which is a relative volatility of 2.9.

EXAMPLE 2

Fifty grams of the 2-pentanone-formic acid azeotrope, 25 grams of cyclohexanone and 25 grams of heptanoic acid were charged to the vapor-liquid equilibrium still and refluxed for 13 hours. Analysis indicated a vapor composition of 66.4% 2-pentanone, 33.6% formic acid and a liquid composition of 56% 2-pentanone, 44% formic acid which is a relative volatility of 1.5. Five grams of cyclohexanone and five grams of heptanoic acid were added and refluxing continued for another 11 hours. Analysis indicated a vapor composition of 54% 2-pentanone, 46% formic acid and a liquid composition of 44.7% 2-pentanone, 55.3% formic acid which is a relative volatility of 1.5.

EXAMPLE 3

Fifty grams of the 2-pentanone-formic acid azeotrope, 17 grams of cyclohexanone, 17 grams of isophorone and 17 grams of methyl benzoate were charged to the vapor-liquid equilibrium still and refluxed for 11 hours. Analysis indicated a vapor composition of 61.6% 2-pentanone, 38.4% formic acid and a liquid composition of 48.7% 2-pentanone, 51.3% formic acid which is relative volatility of 1.7. Three grams each of cyclohexanone, isophorone and methyl benzoate were added and refluxing continued for another 13 hours. Analysis indicated a vapor composition of 68.5% 2-pentanone, 31.5% formic acid and a liquid composition of 48.7% 2-pentanone, 51.3% formic acid which is a relative volatility of 1.7.

EXAMPLE 4

A glass perforated plate rectification column was calibrated with ethylbenzene and p-xylene which possesses a relative volatility of 1.06 and found to have 4.5 theoretical plates. A solution comprising 250 grams of the 2-pentanone-formic acid azeotrope was placed in the stillpot and heated. When refluxing began, an extractive agent comprising 33% cyclohexanone, 33% isophorone and 33% methyl benzoate was pumped into the column at a rate of 20 ml/min. The temperature of the extractive agent as it entered the column was 95° C. After establishing the feed rate of the extractive agent, the heat input to the 2-pentanone-formic acid in the stillpot was adjusted to give a total reflux rate of 10-20 ml/min. After one half hour of operation the overhead and bottoms samples of approximately two ml. were collected and analysed by gas chromatography. The overhead analysis was 96.9% 2-pentanone, 3.1% formic acid. The bottoms analysis was 45.9% 2-pentanone, 54.1% formic acid. Using these compositions in the Fenske equation, with the number of theoretical plates in the column being 4.5, gave an average relative volatility of 1.34 for each theoretical plate. After one hour of continuous operation, the overhead was 97.8% 2-pentanone, 2.2% formic acid and the bottoms was 50% 2-pentanone, 50% formic acid which is a relative volatility of 1.39. After 1.5 hours of continuous operation, the overhead was 98.8% 2-pentanone, 1.2% formic acid and the bottoms was 57.4% 2-pentanone, 42.6% formic acid which is a relative volatility of 1.49.

We claim:

1. A method for recovering 2-pentanone from mixtures of 2-pentanone and formic acid which comprises distilling a mixture of 2-pentanone and formic acid in a rectification column in the presence of about one part of an extractive agent per part of 2-pentanone-formic acid mixture, recovering 2-pentanone as overhead product and obtaining the formic acid and the extractive agent from the stillpot, wherein said extractive agent is a compound selected from the group consisting of cyclohexanone, diisobutylketne, ethyl butylketone, methyl isoamyl ketone, 2-heptanone and 2-octanone.

2. The method of claim 1 in which the extractive agent is diisobutyl ketone.

3. The method of claim 1 in which the extractive agent is ethyl butyl ketone.

4. The method of claim 1 in which the extractive agent is methyl isoamyl ketone.

5. The method of claim 1 in which the extractive agent is 2-heptanone.

6. The method of claim 1 in which the extractive agent is 2-octanone.

7. The method of claim 1 in which the extractive agent is cyclohexanone.

8. A method for recovering 2-pentanone from mixtures of 2-pentanone and formic acid in a rectification column in the presence of about one part of an extractive agent per part of 2-pentanone-formic acid mixture, recovering 2-pentanone as overhead product and obtaining the formic acid and the extractive agent from the stillpot, wherein said extractive agent comprises cyclohexanone and at least one material selected from the group consisting of hexanoic acid, heptanoic acid, isophorone, methyl salicyclate, methyl benzoate, acetophenone and diisobutyl ketone.

9. A method for recovering 2-pentanone from mixtures of 2-pentanone and formic acid which comprises distilling a mixture of 2-pentanone and formic acid in a rectification column in the presence of about one part of an extractive agent per part of 2-pentanone-formic acid mixture, recovering 2-pentanone as overhead product and obtaining the formic acid and the extractive agent from the stillpot, wherein said extractive agent comprises diisobutyl ketone and octanoic acid.

10. A method for recovering 2-pentanone from mixtures of 2-pentanone and formic acid which comprises distilling a mixture of 2-pentanone and formic acid which comprises distilling a mixture of 2-pentanone and formic acid in a rectification column in the presence of about one part of an extractive agent per part of 2-pentanone-formic acid mixture, recovering 2-pentanone as overhead product and obtaining the formic the formic acid and the extractive agent from the stillpot, wherein said extractive agent comprises ethyl butyl ketone and at least one material selected from the group consisting of n-decanoic acid and diethylene glycol dimethyl ether.

* * * * *